(12) United States Patent
Jiang et al.

(10) Patent No.: US 12,127,856 B2
(45) Date of Patent: Oct. 29, 2024

(54) DIFFICULT AIRWAY EVALUATION METHOD AND DEVICE BASED ON MACHINE LEARNING VOICE TECHNOLOGY

(71) Applicant: Shanghai Ninth People's Hospital, Shanghai Jiao Tong University School of Medicine, Shanghai (CN)

(72) Inventors: Hong Jiang, Shanghai (CN); Ming Xia, Shanghai (CN); Ren Zhou, Shanghai (CN); Shuang Cao, Shanghai (CN); Tian Yi Xu, Shanghai (CN); Jie Wang, Shanghai (CN); Chen Yu Jin, Shanghai (CN); Bei Pei, Shanghai (CN)

(73) Assignee: Shanghai Ninth People's Hospital, Shanghai Jiao Tong University School of Medicine, Shanghai (CN)

( * ) Notice: Subject to any disclaimer, the term of this patent is extended or adjusted under 35 U.S.C. 154(b) by 259 days.

(21) Appl. No.: 17/859,001

(22) Filed: Jul. 7, 2022

(65) Prior Publication Data
US 2023/0044289 A1 Feb. 9, 2023

(30) Foreign Application Priority Data
Jul. 27, 2021 (CN) .......................... 202110848963.7

(51) Int. Cl.
*A61B 5/00* (2006.01)
*G10L 25/15* (2013.01)
(Continued)

(52) U.S. Cl.
CPC .......... *A61B 5/7267* (2013.01); *A61B 5/4803* (2013.01); *A61B 5/7257* (2013.01);
(Continued)

(58) Field of Classification Search
None
See application file for complete search history.

(56) References Cited

U.S. PATENT DOCUMENTS

2009/0076814 A1 3/2009 Lee
2010/0312144 A1 12/2010 Connor et al.

FOREIGN PATENT DOCUMENTS

CN 103985390 8/2014
CN 104464744 3/2015
(Continued)

OTHER PUBLICATIONS

Gao in view of Rahman et al., "Continuous Bangla Speech Segmentation using Short-term Speech Features Extraction Approaches," Sep. 1, 2015 (Year: 2015).*

*Primary Examiner* — Richa Sonifrank
*Assistant Examiner* — Jean D. Aristilde
(74) *Attorney, Agent, or Firm* — JCIPRNET

(57) ABSTRACT

The present disclosure relates to a difficult airway evaluation method and device based on a machine learning voice technology. The method includes the following steps: acquiring voice data of a patient; carrying out feature extraction on the voice data, obtaining a pitch period of pronunciations, and acquiring a voiced sound feature and unvoiced sound features based on the pitch period of pronunciations; and constructing a difficult airway evaluation classifier based on the machine learning voice technology, analyzing the received voiced sound feature and unvoiced sound features by the trained difficult airway evaluation classifier, and carrying out scoring on the severity of a difficult airway to obtain an evaluation result of the difficult airway.

7 Claims, 1 Drawing Sheet

(51) Int. Cl.
 *G10L 25/18* (2013.01)
 *G10L 25/21* (2013.01)
 *G10L 25/24* (2013.01)
 *G10L 25/30* (2013.01)
 *G10L 25/45* (2013.01)
 *G10L 25/66* (2013.01)
 *G10L 25/90* (2013.01)
 *G10L 25/93* (2013.01)

(52) U.S. Cl.
 CPC .............. *G10L 25/15* (2013.01); *G10L 25/18* (2013.01); *G10L 25/21* (2013.01); *G10L 25/24* (2013.01); *G10L 25/30* (2013.01); *G10L 25/45* (2013.01); *G10L 25/66* (2013.01); *G10L 25/90* (2013.01); *G10L 25/93* (2013.01)

(56) References Cited

FOREIGN PATENT DOCUMENTS

| | | | | | |
|---|---|---|---|---|---|
| CN | 110910900 | A | * | 3/2020 | ........... G06N 3/0454 |
| CN | 111145786 | A | * | 5/2020 | ........... G06N 3/0454 |
| CN | 212434059 | U | * | 1/2021 | |
| CN | 108269574 | B | * | 5/2021 | ............. G10L 17/02 |
| CN | 114760926 | A | * | 7/2022 | ............. A61B 7/003 |

* cited by examiner

DIFFICULT AIRWAY EVALUATION METHOD AND DEVICE BASED ON MACHINE LEARNING VOICE TECHNOLOGY

CROSS-REFERENCE TO RELATED APPLICATION

This application claims the priority benefit of China application no. 202110848963.7, filed on Jul. 27, 2021. The entirety of the above-mentioned patent application is hereby incorporated by reference herein and made a part of this specification.

FIELD

The present disclosure relates to the field of a computer-aided technology, in particular to a difficult airway evaluation method and device based on a machine learning voice technology.

BACKGROUND

Tracheal intubation is the important means of carrying out airway management on a patient in a general anesthesia state by an anesthetist and takes an important part in the aspects of keeping the airway open, ventilating to supply oxygen, carrying out respiration support, maintaining oxygenation, and the like. However, even though great progress and improvement are made to the tracheal intubation technology and equipment, the intraoperative period complications and the incidence rate of disabilities caused by a difficult airway are not improved very well, particularly for the unpredictable difficult airway. Currently, methods for evaluating the difficult airway generally include Mallampati classification, LEMON scoring, Wilson scoring, auxiliary Computed tomography (CT), Magnetic Resonance Imaging (MRI), Ultrasound (US), and the like, are complex in process and low in positive evaluated value, and all have a certain limitation.

SUMMARY

The present disclosure is to solve the technical problem of providing a difficult airway evaluation method and device based on a machine learning voice technology, so that early warning can be accurately made to a difficult airway in the clinical anesthesia.

In order to solve the technical problem thereof, the present disclosure adopts the technical solution: provided is a difficult airway evaluation method based on a machine learning voice technology, including the following steps:

(1) acquiring voice data of a patient;

(2) carrying out feature extraction on the voice data, obtaining a pitch period of pronunciations, and acquiring a voiced sound feature and unvoiced sound features based on the pitch period of pronunciations; and (3) constructing a difficult airway evaluation classifier based on the machine learning voice technology, analyzing the received voiced sound feature and unvoiced sound features by the trained difficult airway evaluation classifier, and carrying out scoring on the severity of a difficult airway to obtain an evaluation result of the difficult airway.

The voice data acquired in step (1) is voice data capable of reflecting an anatomical structure and a function of the airway.

The voice data in step (1) includes six vowels of /a/, /e/, /i/, /o/, /u/, and /ü/.

The voiced sound feature in step (2) is a formant, and the unvoiced sound features are short-time energy and a short-time average zero crossing ratio.

Acquiring the voiced sound feature in step (2) specifically includes the following steps: carrying out pre-emphasis on an original voice data signal; carrying out windowing and Fourier transform on the pre-emphasized signal; carrying out cepstrum taking on the signal obtained after Fourier transform so as to obtain a cepstrum signal; and carrying out windowing on the cepstrum signal, solving an envelope curve, and obtaining the formant according to a maximum value of the envelope curve.

In step (2), the short-time energy is obtained by $$E_n = \sum_{m=n-N+1}^{\infty} [x(m)w(n-m)]^2,$$

and the short-time average zero crossing ratio is obtained by $$Z_n = \sum_{m=-\infty}^{\infty} |sgn[x(m)] - sgn[x(m-1)]|\omega(m),$$

wherein m represents the ordinal number of a frame, x(m) represents the amplitude of the voice data signal, w(n-m) represents a window function, n represents the frame number, sgn [ ] represents a sign function, and ω(m) represents a proportionality coefficient.

The difficult airway evaluation classifier based on the machine learning voice technology in step (3) is a fully connected neural network, and the fully connected neural network includes one input layer, three hidden layers, and one output layer; and the fully connected neural network has an initial learning rate of 1 and an attenuation rate of 0.0001, a Rectified Linear Unit (ReLU) activation function is adopted, and an optimization function is Stochastic Gradient Descent (SGD).

In order to solve the technical problem thereof, the present disclosure adopts the technical solution that: further provided is a difficult airway evaluation device based on a machine learning voice technology, including: an acquisition module, which is used for acquiring voice data of a patient; a feature extraction module, which is used for carrying out feature extraction on the voice data, obtaining a pitch period of pronunciations, and acquiring a voiced sound feature and an unvoiced sound features based on the pitch period of pronunciations; and an evaluation module, which is used for constructing a difficult airway evaluation classifier based on the machine learning voice technology, analyzing the received voiced sound feature and unvoiced sound features by the trained difficult airway evaluation classifier, and carrying out scoring on the severity of a difficult airway to obtain an evaluation result of the difficult airway.

The feature extraction module includes: a voiced sound feature extraction unit, which is used for carrying out pre-emphasis on an original voice data signal, carrying out windowing and Fourier transform on the pre-emphasized signal, carrying out cepstrum taking on the signal obtained after Fourier transform so as to obtain a cepstrum signal, carrying out windowing on the cepstrum signal, solving an envelope curve, and obtaining a formant according to a maximum value of the envelope curve; and an unvoiced sound feature extraction unit, which is used for obtaining short-time energy by $$E_n = \sum_{m=n-N+1}^{\infty} [x(m)w(n-m)]^2$$

and obtaining a short-time average zero crossing ratio by $$Z_n = \sum_{m=-\infty}^{\infty} |sgn[x(m)] - sgn[x(m-1)]|\omega(m),$$

wherein m represents the ordinal number of a frame, x(m) represents the amplitude of the voice data signal, w(n-m) represents a window function, n represents the frame number, sgn [ ] represents a sign function, and ω(m) represents a proportionality coefficient.

The difficult airway evaluation classifier constructed by the evaluation module is a fully connected neural network, and the fully connected neural network includes one input layer, three hidden layers, and one output layer; and the fully connected neural network has an initial learning rate of 1 and an attenuation rate of 0.0001, a ReLU activation function is adopted, and an optimization function is SGD.

Beneficial Effects

Due to adoption of the technical solutions above, compared to the prior art, the present disclosure has the following advantages and positive effects that: according to the present disclosure, voice feature information is extracted based on the machine learning voice technology, manual measurement is avoided, and the present disclosure has the advantage of automation; and the classifier constructed by a deep learning algorithm is utilized to carry out scoring on the severity of the difficult airway and the overfitting phenomenon is avoided, so that early warning can be accurately made to the difficult airway in the clinical anesthesia.

DETAILED DESCRIPTION OF THE EMBODIMENTS

The present disclosure will be further illustrated below in combination with specific embodiments. It should be understood that those embodiments are merely used for illustrating the present disclosure, but not intended to limit the scope of the present disclosure. In addition, it should be understood that after reading the contents instructed by the present disclosure, those skilled in the art could make various changes or modifications to the present disclosure, and those equivalent forms also shall fall within the scope defined by the appended claims of the present application.

Figure 1:
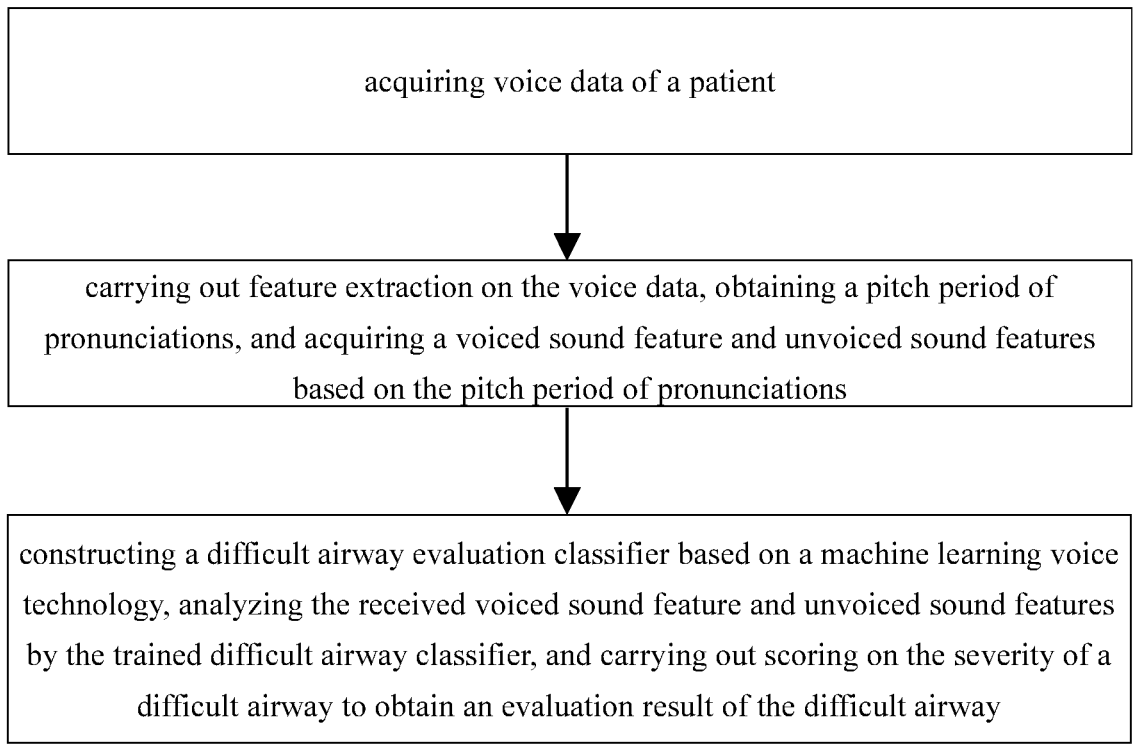
FIG. 1 is a flow chart of an embodiment of the present disclosure.

An embodiment of the present disclosure relates to a difficult airway evaluation method based on a machine learning voice technology, as shown in FIG. 1, including the following steps: voice data of a patient is acquired; feature extraction is carried out on the voice data, a pitch period of pronunciations is obtained, and a voiced sound feature and unvoiced sound features are acquired based on the pitch period of pronunciations; and a difficult airway evaluation classifier is constructed based on the machine learning voice technology, the received voiced sound feature and unvoiced sound features are analyzed by the trained difficult airway evaluation classifier, and scoring is carried out on the severity of a difficult airway to obtain an evaluation result of the difficult airway.

The step that the voice data is acquired specifically includes: the patient is arranged in a fixed quiet consulting room and at the calm sitting position, voice data acquisition is carried out in a Linear Pulse Code Modulation (PCM) format by using a Sony ICD-PX470 voice recorder. The acquired voice data is voice data capable of reflecting an anatomical structure and a function of the airway, and includes six vowels of /a/, /e/, /i/, /o/, /u/, and /ü/. An obtained audio file is output in a WAV format, and obtained audio file data is stored in a confidential database. Acquired contents are 6 vowels and 10 sentences, all the vowels are read as the first tone, the pronunciation is properly prolonged, and the vowels are read at intervals of over one second. The sentences are read at intervals of over two seconds; and intervals in each sentence are smaller than one second.

Voice data arrangement includes: data naming, i.e., voice files of the same human subject are stored in the same folder and the folder is named after a screening number, other information, such as age, gender, height, weight, difficult airway evaluation scale, Cormack-Lehane (CL) grading, and the like, of the patient is stored in the database, and the sequence number corresponds to the name of the voice folder.

Data cleaning includes: samples with incomplete information (voice recording information, intubation information, and the like are missing) are removed, and are arranged into a data set of voice recognition tasks.

Voice feature extraction includes: voice feature extraction in this embodiment is that feature extraction is carried out on the voice data, the pitch period of pronunciations is obtained, and the voiced sound feature and the unvoiced sound features are acquired based on the pitch period of pronunciations.

The glottis enables the vocal cord to generate relaxation oscillation type vibration, and a quasi-periodicity excitation impulse train is generated. Such vocal cord vibration frequency is called as the pitch frequency, and the corresponding period is the pitch period. In this embodiment, firstly, the pitch period of pronunciations needs to be extracted, and then a voiced sound segment and an unvoiced sound segment are distinguished according to the pitch period. The voice data in this embodiment is pronunciations acquired by professional equipment, so a signal is relatively small in noise and relatively pure. For the pure signal, the pitch period may be solved by a cepstrum method, and a specific extraction method is as follows:

$$s[n] = f[n] * \theta[n]$$

$$S(\omega) = \sum_{n=-\infty}^{\infty} s[n]e^{-j\omega n},$$

$$c[n] = \frac{1}{2\pi}\int_{-\pi}^{\pi} \log|S(\omega)|e^{jn\omega}d\omega$$

wherein s [n] represents an original voice data signal and is composed of the amplitude f [n] and the phase θ [n], n represents the number of frames, ω represents the frequency, S (ω) represents the frequency domain signal of the voice data, c [n] represents the frequency spectrum, and the pitch period can be obtained by carrying out peak detection on the frequency spectrum.

After the pitch period is obtained, sound in the pitch period is voiced sound, and on the contrary, sound is unvoiced sound. Various combined shapes of oral cavities and vocal tracts of people cause different formants of pronunciations, under the compound influence of the position of the tongue and the shape of the lips, the vocal organ generates a plurality of resonant frequencies due to vibration, so one sound may have 3 to 5 formants, and the respective meanings are that: a first formant represents the height of the tongue position, a second formant represents the front-back position of the tongue position, a third formant represents the shape of the open lips, and a fourth formant not only represents the tongue, but also represents the lips. A formant extraction method adopted in this embodiment is the cepstrum method, and a specific method is as follows:

The signal is pre-emphasized according to a formula s'[n]=s [n]−a×s [n−1], so that the signal can be subjected to high-frequency promotion and the signal of the glottis is reduced, wherein s [In] represents the original voice data signal, a represents a self-defined parameter and generally is 0.1, and s [n−1] represents a previous frame of signal.

The pre-emphasized signal is windowed and subjected to Fast Fourier Transform (FFT) processing according to a formula $$X(K) = \sum_{n=1}^{N} s'[n]e^{-\frac{2\pi knj}{N}},$$

wherein a window is a Hamming window and N represents a total number of frames.

Cepstrum taking is carried out on X(K) according to a formula $$\hat{x}(n) = \frac{1}{N}\sum_{K=1}^{N} lg|X(K)|e^{-\frac{2\pi knj}{N}}.$$

The cepstrum signal is windowed according to a formula ĥ(n)=x̂(n)×h(n), wherein $n_0$ represents the width of a window function, and $$h(n) = \begin{cases} 1 & n \leq n_0 - 1 \text{ or } n \geq N - n_0 + 1 \\ 0 & n_0 - 1 < n < N - n_0 + 1 \end{cases}, n \in [0, N-1].$$

An envelope curve is solved according to a formula $$H(k) = \sum_{n=1}^{N} \hat{h}(n)e^{-\frac{2\pi knj}{N}},$$

and the corresponding formant can be obtained by solving a maximum value of H(k).

Sound which does not belong to the pitch period is the unvoiced sound, and the production principle of the unvoiced sound is that: when airflow passes through the glottis, the airway is excessively narrow to cause an increase in the airflow speed so as to generate turbulent flow, and finally, the unvoiced sound is produced. Therefore, the unvoiced sound may reflect the width of the airway, and features of the unvoiced sound are represented by short-time energy $E_n$ and a short-time average zero crossing ratio $Z_n$. Specific calculation modes of the features above are as follows:

$$E_n = \sum_{m=n-N+1}^{\infty} [x(m)w(n-m)]^2,$$

wherein m represents the ordinal number of a frame, and x (m) represents the amplitude of the voice data signal;

$$w(n-m) = \begin{cases} 0.54 - 0.46 \times \cos\left[\frac{2\pi(n-m)}{N-1}\right] & 0 \leq n-m \leq N-1 \\ 0 & \text{other} \end{cases},$$

which represents the window function;

$$Z_n = \sum_{m=-\infty}^{\infty} |sgn[x(m)] - sgn[x(m-1)]|\omega(m),$$

wherein sgn [ ] represents a sign function; and $$\omega(m) = \begin{cases} \frac{1}{2N} & 0 \leq n \leq N-1 \\ 0 & \text{other} \end{cases},$$

which represents a proportionality coefficient.

Training set and testing set data splitting and impartiality verification includes: in the training process, training, verification and testing sets are partitioned in advance in a ratio of 80%:10%:10% according to speakers, wherein the training set will be used as an update of a neural network parameter, presentation of an algorithm in the verification set is used as a reference of regulating the learning rate of a neural network; and the testing set is used for evaluating the presentation of a final model.

In this embodiment, the difficult airway evaluation classifier based on the machine learning voice technology is a fully connected neural network, and the fully connected neural network includes five layers in total, including one input layer, three hidden layers, and one output layer; and the fully connected neural network has an initial learning rate of 1 and an attenuation rate of 0.0001, a ReLU activation function is adopted, and an optimization function is SGD. The input of the fully connected neural network includes six features of four formants, the short-time energy $E_n$, and the short-time average zero crossing ratio $Z_n$, the one-hot output is obtained by propagation, and the output corresponds to the C-L intubation difficulty level, and there are four levels in total, wherein when the C-L is the I-II level, it represents that the airway is a non-difficult airway, and when the C-L is the III-IV level, it represents that the airway is a difficult airway. The trained model has a sensitivity of 0.81 for difficult airway evaluation.

It can be seen that the present disclosure utilizes the voice technology to extract voice feature information, manual measurement is avoided, and the present disclosure has the advantage of automation; and the classifier constructed by a deep learning algorithm is utilized to carry out scoring on the severity of the difficult airway and the overfitting phenomenon is avoided, so that early warning can be accurately made to the difficult airway in the clinical anesthesia.

Figure 2:
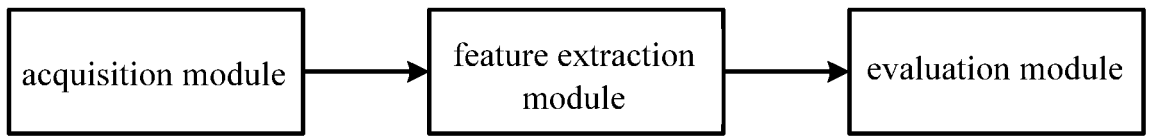
FIG. 2 is a structural schematic diagram of an embodiment of the present disclosure.

An embodiment of the present disclosure further relates to a difficult airway evaluation device based on a machine learning voice technology, as shown in FIG. 2, including: an acquisition module, which is used for acquiring voice data of a patient; a feature extraction module, which is used for carrying out feature extraction on the voice data, obtaining a pitch period of pronunciations, and acquiring a voiced sound feature and unvoiced sound features based on the pitch period of pronunciations; and an evaluation module, which is used for constructing a difficult airway evaluation classifier based on the machine learning voice technology, analyzing the received voiced sound feature and unvoiced sound features by the trained difficult airway evaluation classifier, and carrying out scoring on the severity of a difficult airway to obtain an evaluation result of the difficult airway.

The voice data acquired by the acquisition module is voice data capable of reflecting an anatomical structure and a function of the airway.

The voice data acquired by the acquisition module includes six vowels of /a/, /e/, /i/, /o/, /u/, and /ü/.

The feature extraction module includes: a voiced sound feature extraction unit, which is used for carrying out pre-emphasis on an original voice data signal, carrying out windowing and Fourier transform on the pre-emphasized signal, carrying out cepstrum taking on the signal obtained after Fourier transform so as to obtain a cepstrum signal, carrying out windowing on the cepstrum signal, solving an envelope curve, and obtaining a formant according to a maximum value of the envelope curve; and an unvoiced sound feature extraction unit, which is used for obtaining short-time energy by $$E_n = \sum_{m=n-N+1}^{\infty} [x(m)w(n-m)]^2$$

and obtaining a short-time average zero crossing ratio by $$Z_n = \sum_{m=-\infty}^{\infty} |sgn[x(m)] - sgn[x(m-1)]|\omega(m),$$

wherein m represents the ordinal number of a frame, x(m) represents the amplitude of the voice data signal, w(n-m) represents a window function, n represents the frame number, sgn [ ] represents a sign function, and ω(m) represents a proportionality coefficient.

The difficult airway evaluation classifier constructed by the evaluation module is a fully connected neural network, and the fully connected neural network includes one input layer, three hidden layers, and one output layer; and the fully connected neural network has an initial learning rate of 1 and an attenuation rate of 0.0001, a ReLU activation function is adopted, and an optimization function is SGD.

It is not difficult to find that according to the present disclosure, voice feature information is extracted based on the machine learning voice technology, manual measurement is avoided, and the present disclosure has the advantage of automation; and the classifier constructed by a deep learning algorithm is utilized to carry out scoring on the severity of the difficult airway and the overfitting phenomenon is avoided, so that early warning can be accurately made to the difficult airway in the clinical anesthesia.

What is claimed is:

1. A difficult airway evaluation method based on a machine learning voice technology, comprising:

step (1), acquiring voice data of a patient;

step (2), carrying out feature extraction on the voice data, obtaining a pitch period of pronunciations, and acquiring a voiced sound feature and unvoiced sound features based on the pitch period of pronunciations; wherein the voiced sound feature is a formant, and the unvoiced sound features are short-time energy and a short-time average zero crossing ratio; and step (3), constructing a difficult airway evaluation classifier based on the machine learning voice technology, analyzing the received voiced sound feature and unvoiced sound features by the trained difficult airway evaluation classifier, and carrying out scoring on the severity of a difficult airway to obtain an evaluation result of the difficult airway;

wherein the difficult airway evaluation classifier based on the machine learning voice technology in the step (3) is a fully connected neural network, and the fully connected neural network comprises one input layer, three hidden layers, and one output layer; and the fully connected neural network has an initial learning rate of 1 and an attenuation rate of 0.0001, a Rectified Linear Unit (ReLU) activation function is adopted, and an optimization function is Stochastic Gradient Descent (SGD).

2. The difficult airway evaluation method based on the machine learning voice technology according to claim 1, wherein the voice data acquired in the step (1) is voice data capable of reflecting an anatomical structure and a function of the airway.

3. The difficult airway evaluation method based on the machine learning voice technology according to claim 1, wherein the voice data in the step (1) comprises six vowels of /a/,/e/,/i/,/o/,/u/, and /ü/.

4. The difficult airway evaluation method based on the machine learning voice technology according to claim 1, wherein acquiring the voiced sound feature in the step (2) comprises:

carrying out pre-emphasis on an original voice data signal; carrying out windowing and Fourier transform on the pre-emphasized signal; carrying out cepstrum taking on the signal obtained after Fourier transform so as to obtain a cepstrum signal; and carrying out windowing on the cepstrum signal, solving an envelope curve, and obtaining the formant according to a maximum value of the envelope curve.

5. The difficult airway evaluation method based on the machine learning voice technology according to claim 1, wherein in the step (2), the short-time energy is obtained by $$E_n = \sum_{m=n-N+1}^{\infty} [x(m)w(n-m)]^2,$$

and the short-time average zero crossing ratio is obtained by $$Z_n = \sum_{m=-\infty}^{\infty} |sgn[x(m)] - sgn[x(m-1)]|\omega(m),$$

wherein m represents the ordinal number of a frame, x(m) represents the amplitude of the voice data signal, w(n-m) represents a window function, n represents the frame number, sgn [] represents a sign function, and ω(m) represents a proportionality coefficient.

6. A difficult airway evaluation device based on a machine learning voice technology, comprising:
   an acquisition module, which is used for acquiring voice data of a patient; a feature extraction module, which is used for carrying out feature extraction on the voice data, obtaining a pitch period of pronunciations, and acquiring a voiced sound feature and unvoiced sound features based on the pitch period of pronunciations; and
   an evaluation module, which is used for constructing a difficult airway evaluation classifier based on the machine learning voice technology, analyzing the received voiced sound feature and unvoiced sound features by the trained difficult airway evaluation classifier, and carrying out scoring on the severity of a difficult airway to obtain an evaluation result of the difficult airway;
   wherein the difficult airway evaluation classifier constructed by the evaluation module is a fully connected neural network, and the fully connected neural network comprises one input layer, three hidden layers, and one output layer; and the fully connected neural network has an initial learning rate of 1 and an attenuation rate of 0.0001, a Rectified Linear Unit (ReLU) activation function is adopted, and an optimization function is Stochastic Gradient Descent (SGD).

7. The difficult airway evaluation device based on the machine learning voice technology according to claim 6, wherein the feature extraction module comprises:
   a voiced sound feature extraction unit, which is used for carrying out pre-emphasis on an original voice data signal, carrying out windowing and Fourier transform on the pre-emphasized signal, carrying out cepstrum taking on the signal obtained after Fourier transform so as to obtain a cepstrum signal, carrying out windowing on the cepstrum signal, solving an envelope curve, and obtaining a formant according to a maximum value of the envelope curve;
   and an unvoiced sound feature extraction unit, which is used for obtaining short-time energy by $$E_n = \sum_{m=n-N+1}^{\infty} [x(m)w(n-m)]^2$$

and obtaining a short-time average zero crossing ratio by $$Z_n = \sum_{m=-\infty}^{\infty} |sgn[x(m)] - sgn[x(m-1)]|\omega(m),$$

wherein m represents the ordinal number of a frame, x(m) represents the amplitude of the voice data signal, w(n-m) represents a window function, n represents the frame number, sgn [] represents a sign function, and ω(m) represents a proportionality coefficient.

* * * * *